United States Patent [19]

Commandeur et al.

[11] Patent Number: 5,545,355
[45] Date of Patent: Aug. 13, 1996

[54] DIELECTRIC COMPOSITIONS COMPRISING BENZYLTOLUENE/(METHYLBENZYL) XYLENE ISOMERS

[75] Inventors: Raymond Commandeur, Vizille; Noelle Berger, Ecully; Pierre Jay, Saint-Didier Au Mont D'Or, all of France

[73] Assignee: Atochem, Puteaux, France

[21] Appl. No.: 441,314

[22] Filed: May 15, 1995

Related U.S. Application Data

[63] Continuation of Ser. No. 264,194, Jun. 22, 1994, abandoned, which is a continuation of Ser. No. 943,155, Sep. 10, 1992, abandoned, which is a continuation of Ser. No. 661,175, Feb. 27, 1991, abandoned.

[30] Foreign Application Priority Data

Feb. 27, 1990 [FR] France ................................ 90 02420

[51] Int. Cl.$^6$ ..................................................... C10M 3/10
[52] U.S. Cl. ............................ 252/570; 252/581; 585/25; 585/19; 174/256; 174/236; 361/315; 336/94
[58] Field of Search ................... 252/570, 581; 585/25, 19; 174/25 C, 23 C, 17 CF; 336/84; 361/315, 367

[56] References Cited

U.S. PATENT DOCUMENTS

| | | | |
|---|---|---|---|
| 4,493,943 | 1/1985 | Sato et al. | 174/25 C |
| 4,523,044 | 6/1985 | Commandeur et al. | 585/11 |
| 4,957,815 | 9/1990 | Commandeur et al. | 585/11 |

FOREIGN PATENT DOCUMENTS 299867  12/1988  European Pat. Off. .

*Primary Examiner*—Douglas J. McGinty
*Assistant Examiner*—Necholus Ogden
*Attorney, Agent, or Firm*—Burns, Doane, Swecker & Mathis, L.L.P.

[57] ABSTRACT

Novel dielectric liquids for such electrical components as transformers, capacitors and cables, especially adopted for low temperature applications, comprise a mixture of benzyltoluene and (methylbenzyl)xylene isomers, notably a mixture of benzyltoluene/dibenzyltoluene isomers with (methylbenzyl)xylene/di(methylbenzyl)xylene isomers.

16 Claims, No Drawings

DIELECTRIC COMPOSITIONS COMPRISING BENZYLTOLUENE/(METHYLBENZYL) XYLENE ISOMERS

This application is a continuation, of Application No. 08/264,194, filed Jun. 22, 1994, which is now abounded, which is a continuation, of Application Ser. No. 07/943,155, filed Sep. 10, 1992 which is a continuation application of U.S. Application Ser. No. 07/661,175, filed Feb. 27, 1991, now abandoned Oct. 10, 1992.

BACKGROUND OF THE INVENTION

1. Field of the Invention

The present invention relates to novel dielectric compositions based on benzyltoluene and (methylbenzyl)xylene isomers.

2. Description of the Prior Art

European Patent EP 136,230 describes dielectric compositions essentially comprising a mixture of isomers of benzyltoluene and of dibenzyltoluene, and optionally also containing ditolylphenylmethane.

SUMMARY OF THE INVENTION

It has now unexpectedly been determined that a mixtures of the above known dielectrics with (methylbenzyl)xylene or oligomers of (methylbenzyl)xylene provide improved dielectric compositions that have a particularly low crystallization point. Thus, such novel dielectric compositions are especially adopted for use in outdoor voltage transformers or high-power capacitors.

Briefly, the present invention features novel dielectric compositions especially adopted for low temperature applications and which comprise at least one oligomer of benzyltoluene and at least one oligomer of (methylbenzyl)xylene.

DETAILED DESCRIPTION OF THE PREFERRED EMBODIMENTS OF THE INVENTION

More particularly according to the present invention, by the term "oligomer of benzyltoluene" is intended an isomer or mixture of isomers of formula (A1):

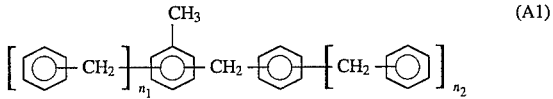

wherein $n_1$ and $n_2 = 0$, 1 or 2, with the proviso that $n_1 + n_2$ is less than or equal to 3.

By the term "oligomer of (methylbenzyl)xylene" is intended an isomer or mixture of isomers of formula (A2):

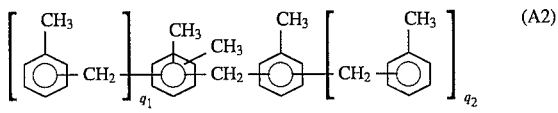

wherein $q_1$ and $q_2 = 0$, 1 or 2, with the proviso that $q_1 + q_2$ is less than or equal to 3.

And by the term "benzyltoluene" is intended oligomer (A1) in which $n_1 + n_2 = 0$, and by "dibenzyltoluene" is intended the oligomer (A1) in which $n_1 + n_2 = 1$. By "(methylbenzyl)xylene" is intended the oligomer (A2) in which $q_1 + q_2 = 0$, and by "di(methylbenzyl)xylene" the oligomer (A2) in which $q_1 + q_2 = 1$.

The compositions according to the invention can thus contain benzyltoluene, dibenzyltoluene and di(methylbenzyl)xylene. Other compositions according to the invention comprise di(methylbenzyl)xylene, product (A2) in which $n_1 + n_2 = 3$, and benzyltoluene, or any other combination thereof, provided that it contains at least one isomer (A1) and at least one isomer (A2). In another embodiment of the invention, the oligomer (A1) can be admixed with an oligomer (B1) which is an isomer, or mixture of isomers of the formula:

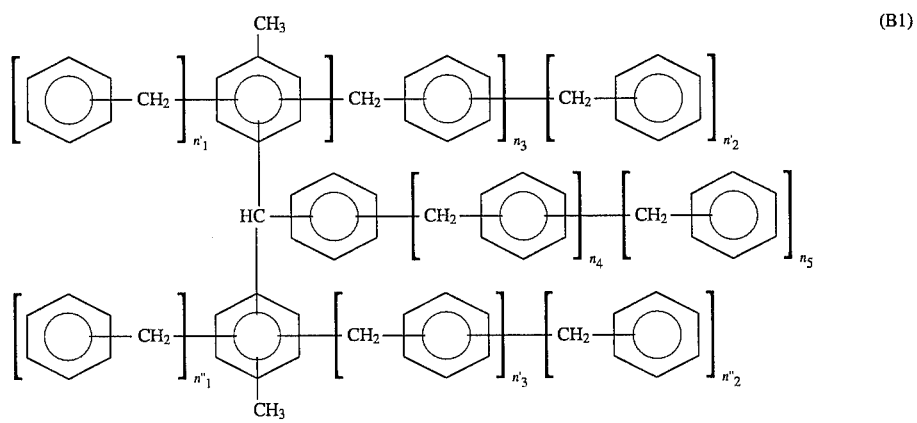

in which $n'_1$, $n''_1$ and $n_4$ are equal to 0, 1 or 2, and $n'_2$, and $n''_2$, $n_3$, $n'_3$ and $n_5$ are equal to 0 or 1, with the proviso that $n'_1 + n''_1 + n'_2 + n''_2 + n_3 + n'_3 + n_4 + n_5$ (represented by the symbol $S_{1n}$) is less than or equal to 2.

The oligomer (A2) can likewise be admixed with an oligomer (B2) which is an isomer or mixture of isomers of the formula:

$$\left[ \underset{CH_3}{\bigcirc} - CH_2 \right]_{q'_1} \left[ \underset{CH_3\ CH_3}{\bigcirc} - CH_2 \right]_{q_3} \left[ \underset{CH_3}{\bigcirc} - CH_2 \right]_{q'_2} \left[ \underset{CH_3}{\bigcirc} \right]_{q'_2}$$ (B2)

$$\left[ \underset{CH_2}{\bigcirc} - CH_2 \right]_{q_4} \left[ \underset{CH_3}{\bigcirc} - CH_2 \right]_{q_5} \left[ \underset{CH_3}{\bigcirc} \right]_{q_5}$$

$$\left[ \underset{CH_3}{\bigcirc} - CH_2 \right]_{q''_1} \left[ \underset{CH_3\ CH_3}{\overset{CH_2}{\bigcirc}} - CH_2 \right]_{q'_3} \left[ \underset{CH_3}{\bigcirc} - CH_2 \right]_{q''_2} \left[ \underset{CH_3}{\bigcirc} \right]_{q''_2}$$

in which $q'_1$, $q''_1$ and $q_4$ are equal to 0, 1 or 2, and $q'_2$, and $q''_2$, $q_3$, $q'_3$ and $q_5$ are equal to 0 or 1, with the proviso that $q'_1+q''_1+q'_2+q''_2+q_3+q'_3+q_4+q_5$ (represented by the symbol $S_{2q}$) is less than or equal to 2.

Such compositions comprising at least 10 parts by weight of product (A2) and 90 parts by weight of product (A1) are particularly advantageous.

The amount of (A2) preferably ranges from 15 to 90 parts by weight from 85 to 10 parts by weight of product (A1).

In another preferred embodiment of the invention, the distribution of the isomers (A1) (in weight %) in the subject compositions ranges from:

60% to 90% for the isomers (A1) wherein $n_1+n_2=0$
5% to 40% for the isomers (A1) wherein $n_1+n_2=1$
0.5% to 8% for the isomers (A1) wherein $n_1+n_2=2$, with the total amounting to 100%.

The above distribution is also applicable to the isomers (A2).

The amount of oligomer (B1) is advantageously at most 15 parts by weight per 100 parts by weight of (A1), and preferably ranges from 2 to 6 parts by weight. This is also applicable to the proportions of (B2) and (A2).

The compositions of the invention are useful dielectrics for capacitors or voltage transformers, or to insulate electrical cables.

The mixtures of isomers (A1) can be prepared by condensing benzyl chloride with toluene in the presence of a catalytically effective amount of a Friedel-Crafts catalyst. It is then only necessary to separate them by distillation.

The mixtures of isomers (A2) can be prepared by condensing methylbenzyl chloride with xylene in the presence of a catalytically effective amount of a Friedel-Crafts catalyst. It is also then only necessary to separate them by distillation.

The oligomers of benzyltoluene (A1) and (B1) can be prepared according to the process described in European Patent EP 136,230, and the oligomers of (methylbenzyl)xylene (A2) and (B2) according to the process described in European Patent EP 299,867. It is then only necessary to admix such oligomers.

For dielectric applications, it is advantageous to purify the compositions of the invention using Fuller's earth or activated alumina, either alone or in combination, according to conditioning techniques known to the art of dielectric liquids.

It can likewise prove advantageous to add stabilizers of the epoxide type thereto, or of another type, such as, for example, tetraphenyltin or anthraquinone compounds.

These additives are typically hydrochloric acid acceptors and are added in amounts usually ranging from 0.001% to 10%, preferably from 0.01% to 0.3% by weight.

Such treatments are per se known to this art. According to the specifications for the dielectrics, it is sometimes necessary to eliminate all of the organic chlorine compounds contained therein to provide compositions having a very low chlorine content, i.e., less than a few ppm. The dechlorination process described in European Patent EP 306,398, assigned to the assignee hereof, is suitable for such purpose.

It too is within the scope of this invention for the subject compositions to be in admixture with other dielectric fluids, for example tetrachlorobenzyltoluene and chlorobenzenes or chlorotoluenes described in European Patent EP 8,251, or mixed with the mineral oils conventionally used in transformers.

In order to further illustrate the present invention and the advantages thereof, the following specific examples are given, it being understood that same are intended only as illustrate and in nowise limitative.

EXAMPLE 1

Measurement of dielectric strengths:

In this example, the measurements were performed using 50 Hz alternating current, at ambient temperature and using bar electrodes $\phi= 0.6$ mm and a Rogowski disc, electrodes $\phi= 40$ mm.

Two types of testing were carried out:

(a) "short" tests, in which the voltage was applied with a 1,000V/s gradient;

(b) "long" tests, in which the voltage was applied in steps, with an increase of 1,000V every 30 seconds.

The results are reported in the following Table:

TABLE

| Inter-electrode distance (mm) | "Short" test | | | "Long" test | | |
|---|---|---|---|---|---|---|
| | PXE | XX01 | BT05/XX05 80/20 | PXE | XX01 | BT05/XX05 80/20 |
| 3.2 | 44.5 kV | 49.9 kV | | 40.2 kV | 43.6 kV | |
| 5 | 55.4 kV | | 84.1 kV | 47.8 kV | 52.5 kV | 57.4 kV |
| 10 | 84.1 kV | | >112 kV | 63.3 kV | 69.5 kV | 77.5 kV |
| 15 | | | | 71.6 kV | 82.4 kV | 105.8 kV |

The numbers reported correspond to average values of 5 to 15 measurements.

In said Table, kV indicates kilovolts;

The values can vary by about 10% from one series of measurements to another; however, the methods permit classification of the various dielectrics;

(i) PXE denotes a dielectric, not according to the invention, which is a mixture of isomers of 1-phenyl-1-xylylethane of the formula:

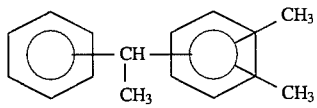

(ii) XX01 denotes a dielectric of formula (A2) in which $q_1$ and $q_2$ are equal to 0 (methylbenzylxylene);

(iii) BT05 denotes a mixture of:

85 parts by weight of isomers of formula (A1) wherein $n_1+n_2=0$, benzyltoluene;

11 parts by weight of isomers of formula (A1) wherein $n_1+n_2=1$, dibenzyltoluene;

4 parts of oligomers (B1) with $S_{1n}=0$.

The amount of (B1) was thus 4 parts by weight to 96 parts by weight of (A1).

(iv) XX05 denotes a mixture of:

85 parts by weight of isomers of formula (A2) wherein $q_1+q_2=0$;

11 parts by weight of isomers of formula (A2) wherein $q_1+q_2=1$;

4 parts by weight of oligomers of formula (B2) wherein $S_{2q}=0$;

(v) BT05/XX05 80/20 denotes a mixture of 80 parts by weight of BT05 and 20 parts by weight of XX05; namely, the mixture according to the invention contained:

0.8 × (85+11) parts by weight of (A1) to 0.2 × (85+11) parts by weight of (A2), i.e., 76.8 parts by weight of (A1) to 19.2 parts by weight of (A2).

EXAMPLE 2

Crystallization tests:

Liquids tested:

(i) BT06: (a): 79 parts by weight of (A1) wherein $n_1+n_2=0$ 16 parts by weight of (A1) wherein $n_1+n_2=1$, and 5 parts by weight of (B1) wherein $S_n=0$;

(ii) BT01: (b) : product (A1) wherein $n_1+n_2=0$ (benzyltoluene);

(iii) XX01: (c) : (A2) wherein $q_1+q_2=0$;

(iv) XX05: (d): cf. Example 1;

(v) mixtures:

BT01+XX01: (e): 25-50-75 weight %,

BT06+XX01: (f): 25-50-75 weight %,

BT06+XX05: (g): 25-50-75 weight %,

BT05+XX05: (h): 5-10-15-20-25-30 weight % of XX05;

(vi) SAS-40: (i) : product of Nippon Petrochemical based on BT01 and diphenylethane;

(vii) SCF 150: (j): product of Sybron=ditolylmethane.

Progress of the tests:

(1) Cycles −20°/−30° .C on b, c, e, f→no crystallization;

(2) Cycles −30°/−40° C.→

After 4 days, BT01 and XX01 completely crystallized, and were used for seeding other mixtures After 8 days:

(i) mixtures of BT06 or BT01+75% XX01=crystallized, (ii) mixtures of BT06 or BT01+50% XX01=some crystals, (iii) mixtures of BT06 or BT01+25% XX01: no crystallization.

(3) Cycles −40°/−45° C→

After 8 days, introduction of a, g, d, i, seeded the next day

After 12 days:

(i) mixtures of BT06 or BT01+50% XX01: about ⅓ crystallized, (ii) BT01+25% XX01: some crystals, (iii) BT06: some crystals over about ⅔ of the tube, (iv) BT06+XX01 (25%): no crystallization, (v) XX05: no crystallization, (vi) mixtures of BT06+XX05: no crystallization, (vii) SAS-40: no crystallization.

(4) Cycles −45°/−50° C. for 14 days→

(i) BT06: some crystals over ⅔ of the tube, (ii) mixtures of BT06 or BT01+50% XX01: crystals in the entirety of the tube, (iii) BT01+25% XX01: some crystals, (iv) SAS-40: some crystals, (v) BT06+25% XX01: no crystallization, (vi) XX05 and mixtures of BT06+XX05: no crystallization.

(5) Cycles −50°/−60° C. for 6 days (introduction of j):

(i) BT06: some crystals in the entirety of the tube, but liquid matrix, (ii) mixtures with 50% XX01: idem BT06, (iii) SCF 150: completely crystallized (after one night), (vi) BT01+25% XX01: some crystals, (v) SAS-40: some crystals, (vi) BT06+25% XX01: no crystallization, (vii) XX05 and mixtures of BT06+XX05: no crystallization.

(6) Return to cycles -40/45° C: introduction of h after 4 days:
(i) SCF 150: completely crystallized,
(ii) BT01, XX01, and mixtures of BT01 or BT06 +75% XX01: crystallized,
(iii) BT06 and mixtures of BT01 or BT06+50 50% XX01: melting of a portion of the crystals,
(iv) BT01+25% XX01: some crystals,
(V) SAS-40: some crystals,
(vi) the remainder: no crystals.

EXAMPLE 3

A second series of crystallization tests was carried out, maintaining the temperature at −50° C. for 43 days. All of the tubes had been "seeded" with crystals of BT01.
(i) SAS-40: crystals in the entirety of the tube,
(ii) mixtures of BT06 and XX05 (in parts)
(a) 100/0: crystals over ⅓ of the tube,
(b) 95/5: crystals over ⅓ of the tube,
(c) 90/10: ⅔ of the tube crystallized,
(d) 85/15: ⅓ of the tube contained crystals,
(e) 80/20: very few crystals
(iii) mixtures of BT05 and XX05 (in parts by weight):
(a) 95/5: crystals over ⅓ of the tube,
(b) 90/10: some crystals in the entirety of the tube,
(c) 85/15: crystals precipitated in the bottom of the tube (about ¼ volume),
(d) 80/20: some crystals at the bottom of the tube,
(e) 75/25: no crystallization,
(f) 70-30: no crystallization.

While the invention has been described in the terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A composition of matter adopted for dielectric applications, comprising a mixture of (a) a dielectrically effective amount of at least one isomer of benzyltoluene having the formula (A1):

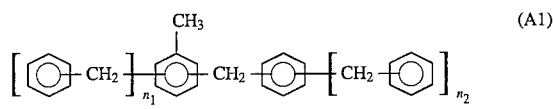

wherein $n_1$ and $n_2$=0, 1 or 2, with the proviso that $n_1+n_2$ is less than or equal to 3; and (b) a dielectrically effective amount of at least one isomer of (methylbenzyl)xylene having the formula (A2):

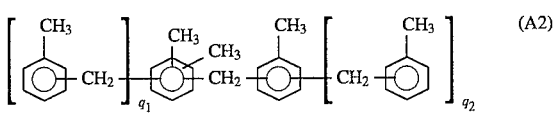

wherein $q_1$ and $q_2$=0, 1 or 2, with the proviso that $q_1+q_2$ is less than or equal to 3, wherein said isomers A1 and A2 are present in proportions ranging from about 90/10 to about 70/30.

2. The composition of matter as defined by claim 1, further comprising a dielectrically effective amount of at least one isomer having the formula (B1):

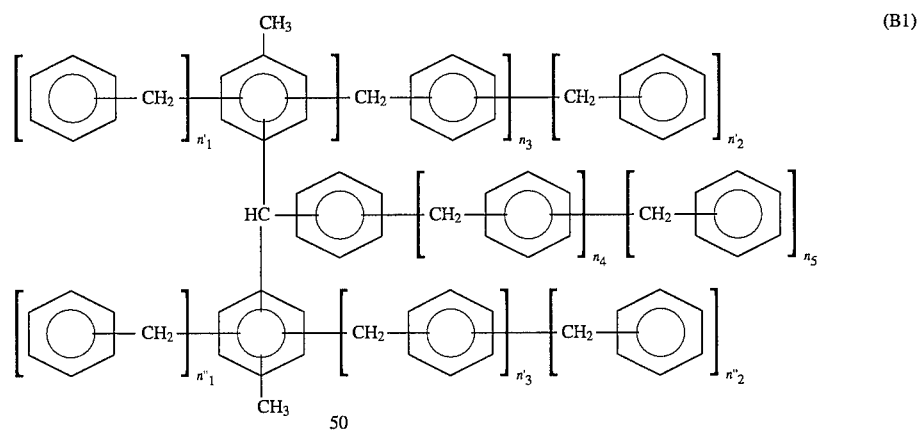

wherein $n'_1$, $n''_1$ and $n_4$ are equal to 0, 1 or 2, and $n'_2$, $n''_2$, $n_3$, $n'_3$ and $n_5$ are equal to 0 or 1, with the proviso that $n'_1+n''_1+n'_2+n''_2+n_3+n''_3+n_4+n_5$ (designated $S_{1n}$) is less than or equal to 2.

3. The composition of matter as defined by claim 1, further comprising a dielectrically effective amount of at least one isomer having the formula (B2):

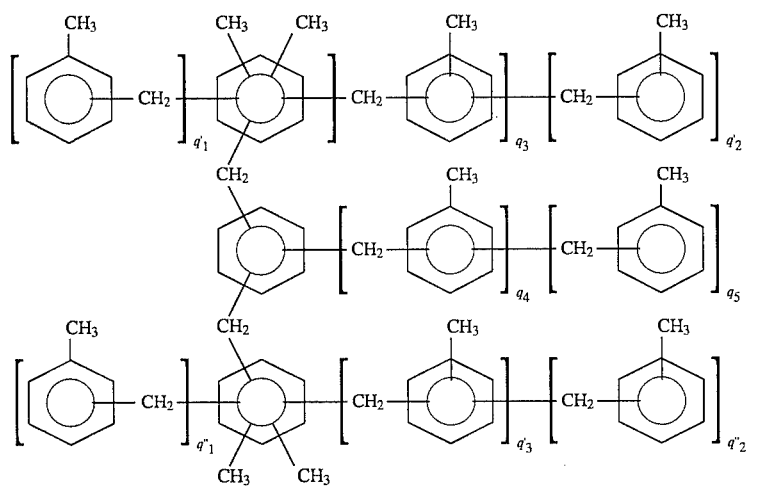
(B2)

wherein $q''_1$, $q''_1$ and $q_4$ are equal to 0, 1 or 2, and $q'_2$ $q''_2$, $q_3$, $q'_3$ and $q_5$ are equal to 0 or 1, with the proviso that $q'_1+q''_1+q'_2+q''_2+q_3+q'_3+q_4+q_5$ (designated $S_{2q}$) is less than 2.

4. A composition of matter adopted for dielectric applications, comprising a mixture of (a) a dielectrically effective amount of at least one isomer of benzyltoluene having the formula (A1):

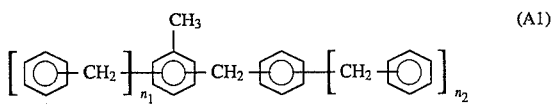
(A1)

wherein $n_1$ and $n_2$=0, 1 or 2, with the proviso that $n_1+n_2$ is less than or equal to 3; and (b) a dielectrically effective amount of at least one isomer of (methylbenzyl)xylene having the formula (A2):

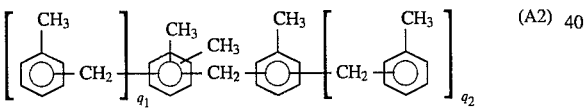
(A2)

wherein $q_1$ and $q_2$=0, 1 or 2, with the proviso that $q_1+q_2$ is less than or equal to 3, wherein said isomers A1 and A2 are present in proportions sufficient to provide a composition more resistant to crystallization than either $A_1$ or $A_2$ alone, and which comprises about 10-30 parts by weight of isomers (A2) per about 90-70 parts by weight of isomers (A1).

5. The composition of matter as defined by claim 4, comprising from 15 to 90 parts by weight of isomers (A2) per 85 to 10 parts by weight of isomers (A1).

6. A composition of matter adapted for dielectric applications, comprising a mixture of (a) a dielectrically effective amount of at least one isomer of benzyltoluene having the formula (A1);

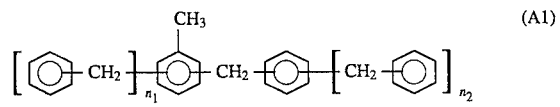
(A1)

wherein $n_1$ and $n_2$=0, 1 or 2, with the proviso that $n_1+n_2$ is less than or equal to 3; and (b) a dielectrically effective amount of at least one isomer of (methylbenzyl)xylene having the formula (A2);

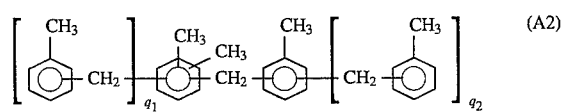
(A2)

wherein $q_1$ and $q_2$=0, 1 or 2, with the proviso that $q_1+q_2$ is less than or equal to 3, wherein said isomers A1 and A2 are present in proportions ranging from about 90/10 to about 70/30 wherein from 60% to 90% by weight of said benzyltoluene isomers (A1) are such that $n_1+n_2$=0, from 5% to 40% by weight of said benzyltoluene isomers (A1) are such that $n_1+n_2$=1, and from 0.5% to 8% by weight of said benzyltoluene isomers (A1) are such that $n_1+n_2$= 2.

7. A composition of matter adapted for dielectric applications, comprising a mixture of (a) a dielectrically effective amount of at least one isomer of benzyltoluene having the formula (A1):

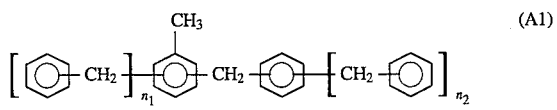
(A1)

wherein $n_1$ and $n_2$=0, 1 or 2, with the proviso that $n_1+n_2$ is less than or equal to 3; and (b) a dielectrically effective amount of at least one isomer of (methylbenzyl)xylene having the formula (A2)

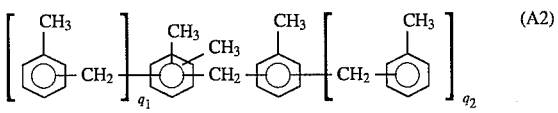
(A2)

wherein $q_1$ and $q_2$=0, 1 or 2, with the proviso that $q_1+q_2$ is less than or equal to 3, wherein said isomers A 1 and A2 are present in proportions, ranging from about 90/10 to about 70/30 alone, wherein from 60% to 90% by weight of said (methylbenzyl)xylene isomers (A2) are such that $q_1+q_2$=0, from 5% to 40% by weight of said (methylbenzyl)xylene isomers (A2) are such that $q_1+q_2$=1, and from 0.5% to 8% by weight of said (methylbenzyl)xylene isomers (A2) are such that $q_1+q_2$=2.

8. A composition of matter adapted for dielectric applications, comprising a mixture of (a) a dielectrically effective amount of at least one isomer of benzyltoluene having the formula (A1):

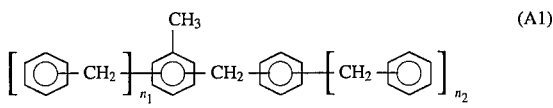

(A1)

wherein $n_1$ and $n_2$=0, 1 or 2, with the proviso that $n_1+n_2$ is less than or equal to 3; and (b) a dielectrically effective amount of at least one isomer of (methylbenzyl)xylene having the formula (A2):

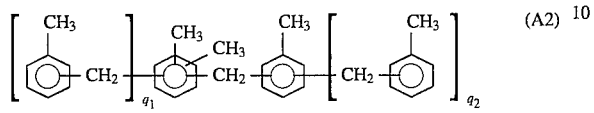

(A2)

wherein $q_1$ and $q_2$=1 or 2, with the proviso that $q_1+q_2$ is less than or equal to 3, and further comprising a dielectrically effective amount of at least one isomer having the formula (B1):

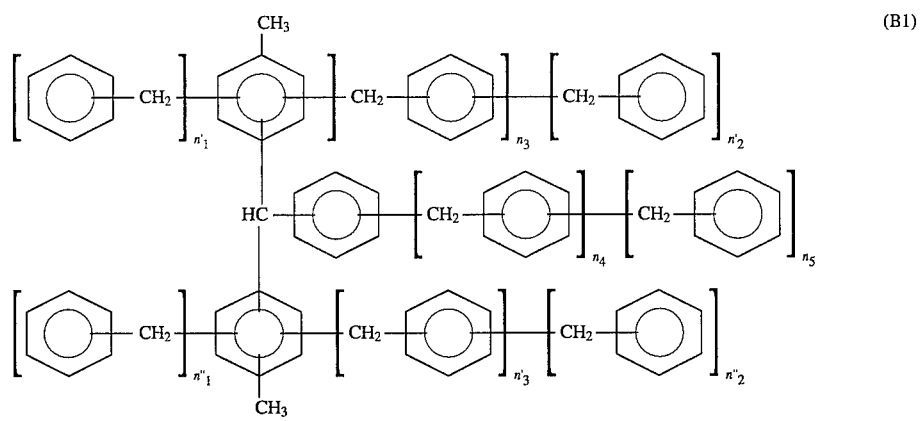

wherein $n'_1$, $n''_1$ and $n_4$ are equal to 0, 1 and 2, and $n'_{2l}$, $n''_2$, $n_3$, $n'_3$ and $n_5$ are equal to 0 or 1, with the proviso that $n'_1+n''_1+n'_2+n''_2+n_3+n'_3+n_4+n_5$ (designated $S_{1n}$) is less than or equal to 2. wherein said isomers A1 and A2 are present in proportions ranging from about 90/10 to about 70/30 and which comprises up to 15 pans by weight of said isomers (B1) per 100 pans by weight of said benzyltoluene isomers (A1).

9. The composition of matter as defined by claim 8, comprising from 2 to 6 parts by weight of said isomers (B1).

10. A composition of matter adapted for dielectric applications, comprising a mixture of (a) a dielectrically effective amount of at least one isomer of benzyltoluene having the formula (A1):

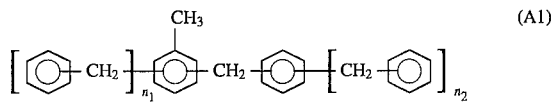

(A1)

wherein $n_1$ and $n_2$=0, 1 or 2, with the proviso that $n_1+n_2$ is less than or equal to 3; and (b) a dielectrically effective amount of at least one isomer of (methylbenzyl)xylene having the formula (A2):

(A2)

wherein $q_1$ and $q_2$=0, 1 or 2, with the proviso that $q_1+q_2$ is less than or equal to 3 and further comprising a dielectrically effective amount of at least one isomer having the formula (B2):

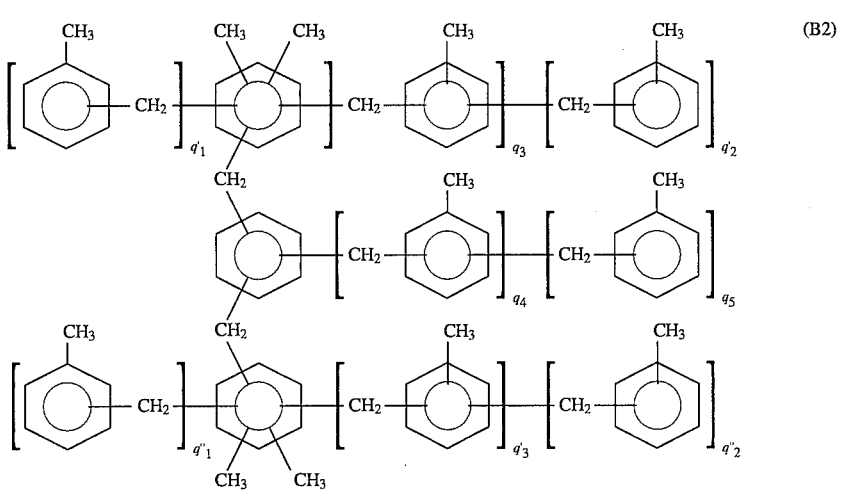

(B2)

wherein said isomers A1 and A2 are present in proportions ranging from about 90/10 to about 70/30 and which comprises up to 15 parts by weight of said isomers (B2) per 100 parts by weight of said (methylbenzyl)xylene isomers (A2).

11. The composition of matter as defined by claim 10, comprising from 2 to 6 parts by weight of said isomers (B2).

12. The composition of matter as defined by claim 2, further comprising a dielectrically effective amount of at least one isomer having the formula (B2):

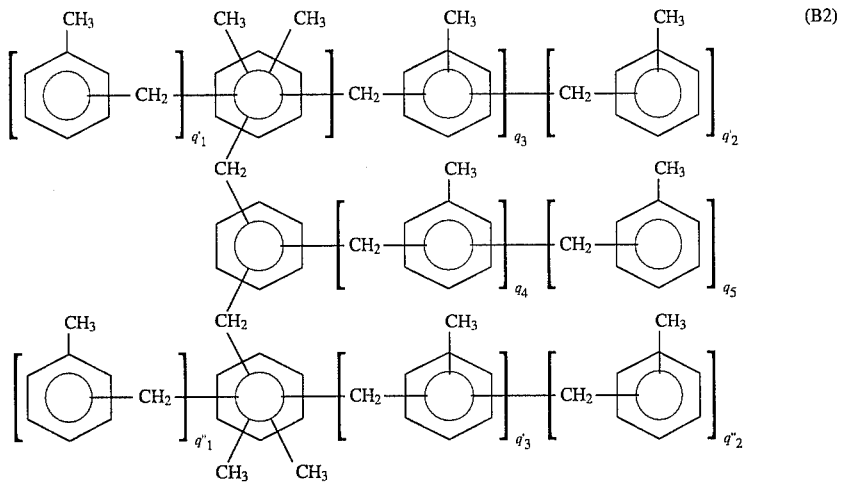

wherein $q'_1$, $q''_1$ and $q_4$ are equal to 0, 1 or 2, and $q'_2$, $q''_2$, $q_3$, $q'_3$ and $q_5$ are equal to 0 or 1, with the proviso that $q'_1+q''_1+q'_2+q''_2+q_3+q'_3+q_4+q_5$ (designated $S_{2q}$) is equal to or less than 2.

13. The composition of matter as defined by claim 1, further comprising a hydrochloric acid acceptor.

14. The composition of matter as defined by claim 1, further comprising a tetrachlorobenzyltoluene, chlorobenzene or chlorotoluene.

15. In an electrical component including a dielectric liquid, the improvement which comprises, as the dielectric liquid therefor, a dielectrically effective amount of the composition of matter as defined by claim 1.

16. The electrical component as defined by claim 15, comprising a capacitor, transformer or cable.

* * * * *